US010206646B2

(12) United States Patent
Gulsun et al.

(10) Patent No.: US 10,206,646 B2
(45) Date of Patent: Feb. 19, 2019

(54) METHOD AND SYSTEM FOR EXTRACTING CENTERLINE REPRESENTATION OF VASCULAR STRUCTURES IN MEDICAL IMAGES VIA OPTIMAL PATHS IN COMPUTATIONAL FLOW FIELDS

(71) Applicant: Siemens Healthcare GmbH, Erlangen (DE)

(72) Inventors: Mehmet Akif Gulsun, Lawrenceville, NJ (US); Yefeng Zheng, Princeton Junction, NJ (US); Saikiran Rapaka, Pennington, NJ (US); Viorel Mihalef, North Brunswick, NJ (US); Puneet Sharma, Monmouth Junction, NJ (US); Gareth Funka-Lea, Cranbury, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 225 days.

(21) Appl. No.: 15/453,229

(22) Filed: Mar. 8, 2017

(65) Prior Publication Data
US 2017/0258433 A1    Sep. 14, 2017

Related U.S. Application Data

(60) Provisional application No. 62/306,453, filed on Mar. 10, 2016, provisional application No. 62/306,434, (Continued)

(51) Int. Cl.
*G06K 9/00* (2006.01)
*A61B 6/00* (2006.01)
(Continued)

(52) U.S. Cl.
CPC ............ *A61B 6/5217* (2013.01); *A61B 6/504* (2013.01); *A61B 6/507* (2013.01); *G06K 9/4623* (2013.01);
(Continued)

(58) Field of Classification Search
None
See application file for complete search history.

(56) References Cited

U.S. PATENT DOCUMENTS

| 5,701,898 A * | 12/1997 | Adam | A61B 8/06 600/454 |
| 6,535,835 B1 * | 3/2003 | Rubin | A61B 8/06 702/159 |

(Continued)

OTHER PUBLICATIONS

Bouix, Sylvain, Kaleem Siddiqi, and Allen Tannenbaum. "Flux driven automatic centerline extraction." Medical image analysis 9.3 (2005): 209-221. (Year: 2005).*

(Continued)

*Primary Examiner* — Bhavesh M Mehta
*Assistant Examiner* — Samah A Beg

(57) ABSTRACT

A method and apparatus for extracting centerline representations of vascular structures in medical images is disclosed. A vessel orientation tensor for each of a plurality of voxels associated with the target vessel, such as a coronary artery, in a medical image, such as a coronary tomography angiography (CTA) image, using a trained vessel orientation tensor classifier. A flow field is estimated for the plurality of voxels associated with the target vessel in the medical image based on the vessel orientation tensor estimated for each of the plurality of voxels. A centerline of the target vessel is extracted based on the estimated flow field for the plurality of vessels associated with the target vessel in the medical image by detecting a path that carries maximum flow.

31 Claims, 15 Drawing Sheets

Related U.S. Application Data filed on Mar. 10, 2016, provisional application No. 62/306,459, filed on Mar. 10, 2016.

(51) Int. Cl.
*G06T 7/00* (2017.01)
*G06T 13/20* (2011.01)
*G06T 11/20* (2006.01)
*G06T 7/73* (2017.01)
*G06K 9/46* (2006.01)
*G06K 9/62* (2006.01)

(52) U.S. Cl.
CPC ............ *G06K 9/627* (2013.01); *G06T 7/0012* (2013.01); *G06T 7/73* (2017.01); *G06T 11/206* (2013.01); *G06T 13/20* (2013.01); *G06K 2009/00932* (2013.01); *G06K 2009/00939* (2013.01); *G06K 2209/05* (2013.01); *G06T 2207/20076* (2013.01); *G06T 2207/30104* (2013.01)

(56) References Cited

U.S. PATENT DOCUMENTS

| | | | |
|---|---|---|---|
| 7,916,919 B2 | 3/2011 | Zheng et al. | |
| 7,953,266 B2* | 5/2011 | Gulsun | G06K 9/4638 |
| | | | 382/131 |
| 7,990,379 B2 | 8/2011 | Aharon et al. | |
| 7,993,274 B2* | 8/2011 | Pruvot | A61B 8/12 |
| | | | 382/131 |
| 8,488,852 B2 | 7/2013 | Gupta et al. | |
| 8,582,854 B2* | 11/2013 | Zhang | G06K 9/00 |
| | | | 382/130 |
| 8,675,943 B2 | 3/2014 | Zheng et al. | |
| 9,129,417 B2* | 9/2015 | Zheng | G06T 7/66 |
| 2006/0050941 A1 | 3/2006 | Middleton et al. | |
| 2010/0014739 A1* | 1/2010 | Kiraly | G06K 9/342 |
| | | | 382/131 |
| 2010/0076296 A1 | 3/2010 | Mittal et al. | |
| 2010/0239148 A1* | 9/2010 | Zheng | G06K 9/4638 |
| | | | 382/131 |
| 2010/0303358 A1* | 12/2010 | Acharyya | A61B 5/7264 |
| | | | 382/190 |
| 2012/0078106 A1* | 3/2012 | Dentinger | A61B 8/06 |
| | | | 600/454 |
| 2013/0216110 A1 | 8/2013 | Zheng et al. | |
| 2013/0226003 A1* | 8/2013 | Edic | A61B 6/504 |
| | | | 600/454 |
| 2014/0147013 A1* | 5/2014 | Shandas | A61B 8/481 |
| | | | 382/107 |
| 2015/0235360 A1* | 8/2015 | Zheng | G06K 9/46 |
| | | | 382/128 |
| 2015/0238148 A1* | 8/2015 | Georgescu | A61B 5/7267 |
| | | | 600/408 |
| 2016/0217586 A1* | 7/2016 | Dickrell, III | G06T 7/11 |
| 2016/0228000 A1* | 8/2016 | Spaide | G06T 15/08 |
| 2016/0278725 A1* | 9/2016 | Van Nijnatten | A61B 6/481 |
| 2017/0262733 A1* | 9/2017 | Gulsun | G06K 9/4628 |
| 2017/0262981 A1* | 9/2017 | Gulsun | G06K 9/6256 |
| 2017/0270705 A1* | 9/2017 | Hopfgartner | A61B 6/032 |
| 2017/0309015 A1* | 10/2017 | Fleming | G06T 7/70 |

OTHER PUBLICATIONS

çetin, Süheyla, et al. "Vessel tractography using an intensity based tensor model." Miccai Conference, 2011. (Year: 2011).*

Gülsün, Mehmet A., et al. "Coronary centerline extraction via optimal flow paths and CNN path pruning." International Conference on Medical Image Computing and Computer-Assisted Intervention. Springer, Cham, 2016. (Year: 2016).*

Hassouna, M. Sabry, and Aly A. Farag. "Robust centerline extraction framework using level sets." Computer Vision and Pattern Recognition, 2005. CVPR 2005. IEEE Computer Society Conference on. vol. 1. IEEE, 2005. (Year: 2005).*

Johnston, Barbara M., et al. "Non-Newtonian blood flow in human right coronary arteries: steady state simulations." Journal of biomechanics 37.5 (2004): 709-720. (Year: 2004).*

\* cited by examiner 100         110

500    510    520

700

710

900 910

1300 1310

METHOD AND SYSTEM FOR EXTRACTING CENTERLINE REPRESENTATION OF VASCULAR STRUCTURES IN MEDICAL IMAGES VIA OPTIMAL PATHS IN COMPUTATIONAL FLOW FIELDS

This application claims the benefit of U.S. Provisional Application No. 62/306,453, filed Mar. 10, 2016, U.S. Provisional Application No. 62/306,434, filed Mar. 10, 2016, and U.S. Provisional No. 62/306,459, filed Mar. 10, 2016, the disclosures of which are herein incorporated by reference.

BACKGROUND OF THE INVENTION

The present invention relates to extracting a centerline representation of vascular branches in medical images, and more particularly, to automated centerline extraction of vascular branches in medical images via optimal paths in computational flow fields.

Automatic segmentation of coronary arteries in Computed Tomography Angiography (CTA) facilitates the diagnosis, treatment, and monitoring of coronary artery diseases. An important step in coronary artery segmentation is to extract a curve along the center of the coronary artery referred to as a centerline. A centerline representation is important for the visualization of the artery through a curved planar reformatting. A centerline is also useful to support lumen segmentation methods for quantitative assessments, such as stenosis grading or CT based Fractional Flow Reserve (FFR) measurements.

Coronary arteries constitute only a small portion of a large CTA volume because of their thin and longitudinal geometry, and segmentation of coronary arteries is not an easy task due to nearby heart tissues and other vessels such as veins. Most existing centerline tracing techniques for extracting coronary artery centerlines are based on minimal path extraction algorithms that are very prone to making shortcuts through non-coronary structures due to imaging artifacts and contrast variation, severe pathologies, and sharp or fuzzy bifurcations. Methods have been proposed to compute "vesselness" masks with very high sensitivity. However, such vesselness masks may still include false positive voxels belonging to background or nearby structures, causing the centerline extraction to make connections through false positive voxels.

BRIEF SUMMARY OF THE INVENTION

The present invention provides a method and system for extracting centerlines of vascular structures in medical images using optimal paths in computational flow fields computed in the vascular structures. Embodiments of the present invention can be utilized for extracting coronary artery centerlines in computed tomography angiography (CTA) images. Embodiments of the present invention utilize an analogy of fluid flowing from regions of high pressure to those of low pressure by setting up a fluid flow problem where the coronary ostium is specified as a high pressure region. Embodiments of the present invention extract vascular centerlines using the computed flow fields by finding optimal paths that maximize the flow carried along the paths.

In one embodiment of the present invention, a vessel orientation tensor is estimated for each of a plurality of voxels associated with the target vessel in the medical image using a trained vessel orientation tensor classifier. A flow field is estimated for the plurality of voxels associated with the target vessel in the medical image based on the vessel orientation tensor estimated for each of the plurality of voxels. A centerline of the target vessel is extracted based on the estimated flow field for the plurality of vessels associated with the target vessel in the medical image by detecting a path that carries maximum flow.

These and other advantages of the invention will be apparent to those of ordinary skill in the art by reference to the following detailed description and the accompanying drawings.

DETAILED DESCRIPTION

The present invention relates to a method and system for extracting centerlines of vascular structures in medical images via optimal paths in computational flow fields. Embodiments of the present invention are described herein to give a visual understanding of the vascular centerline extraction method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Figure 1:
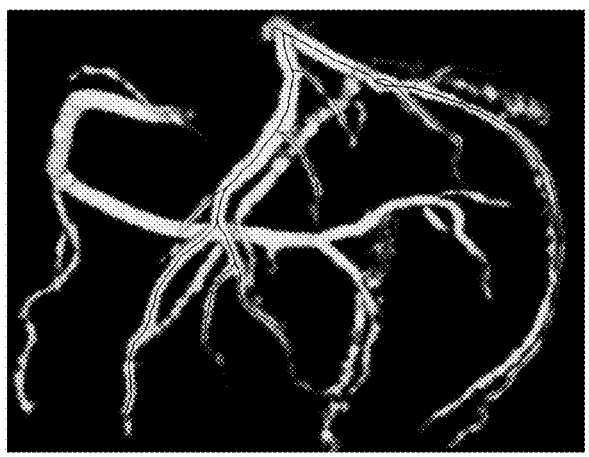
FIG. 1 illustrates exemplary centerline detection results using a minimal path extraction algorithm.
Figure 1:
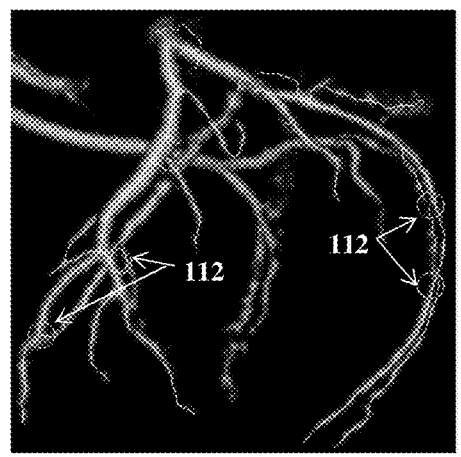

Coronary arteries constitute only a small portion of a large CTA volume because of their thin and longitudinal geometry. The extraction of coronary artery centerlines is challenging due to nearby heart tissues and other vessels such as veins. The majority of the existing centerline tracing techniques are based on minimal path extraction algorithms that compute paths between locations by minimizing a vesselness or medialness cost metric along the path. However, these methods are very sensitive to the cost metric and can easily make shortcuts if the cost is high along the true path which is likely for coronaries due to pathologies or imaging artifacts. In addition, cost cumulative property of these methods makes them sensitive to the length of the path and favor shorter paths. Methods have been proposed to compute "vesselness" masks to separate coronaries from other structures with very high sensitivity. However, such vesselness masks may still include false positive voxels belonging to background or nearby touching structures, causing centerline extraction techniques to make connections through false positive voxels. FIG. 1 illustrates exemplary centerline detection results using a minimal path extraction algorithm. As shown in FIG. 1, image 100 shows an exemplary coronary vesselness mask overlaid with ground truth left coronary artery centerlines. It can be observed that the coronary vesselness mask 100 includes false positive voxels belonging to background and veins adjacent to the coronary arteries. Image 110 shows coronary artery centerlines extracted using a shortest path algorithm overlaid on the coronary vesselness mask 100. As shown in image 110, the extracted coronary artery centerlines make frequents shortcuts 112 between adjacent vessel branches.

Embodiments of the present invention perform vessel centerline tracing by extracting maximum flow paths in computational flow fields. In contrast to conventional centerline extraction techniques, embodiments of the present invention are not based on minimal paths and are less prone to shortcut issues that result in extraction of inaccurate vessel centerlines. Embodiments of the present invention formulate the centerline extraction problem as finding maximum flow paths in steady state porous media flow. Embodiments of the present invention perform machine learning based estimation of anisotropic vessel orientation tensors and use the estimated vessel orientation tensors as permeability for flow computations. Embodiments of the present invention utilize a trained deep neural network (e.g., convolutional neural network (CNN)) branch classifier to distinguish true detected centerlines from leakage. Embodiments of the present invention utilize model-based coronary specific territories and main branches for improved accuracy and runtime in extraction of coronary artery centerlines.

Figure 2:
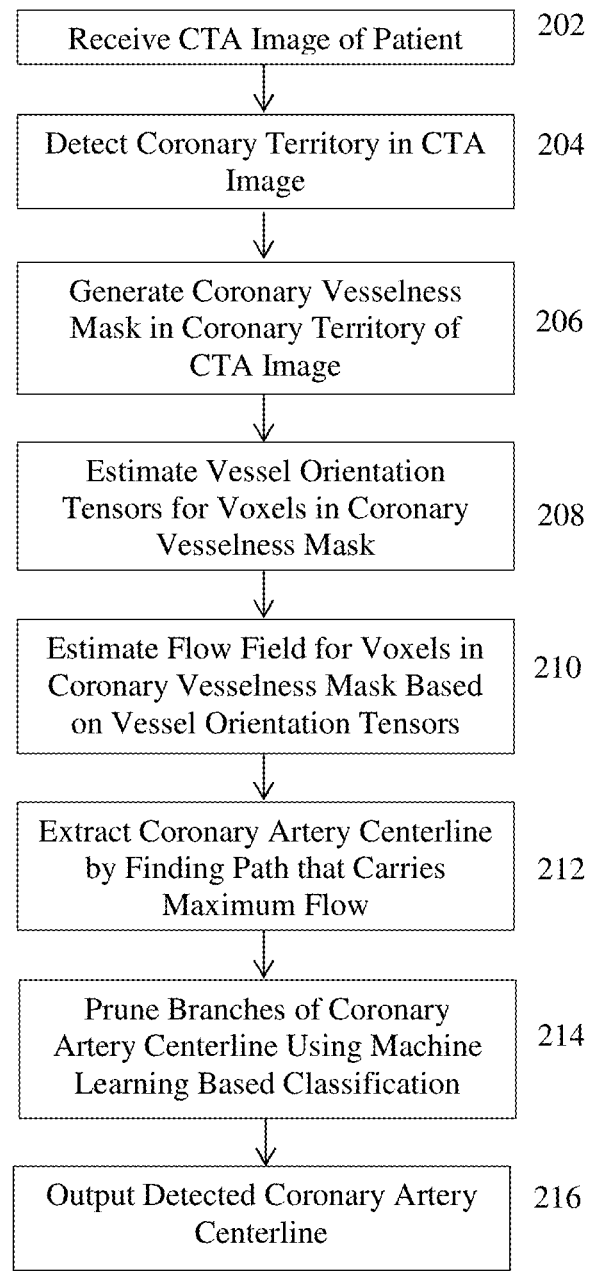
FIG. 2 illustrates a method of extracting coronary artery centerlines from a computed tomography angiography (CTA) image according to an embodiment of the present invention.
Figure 3:
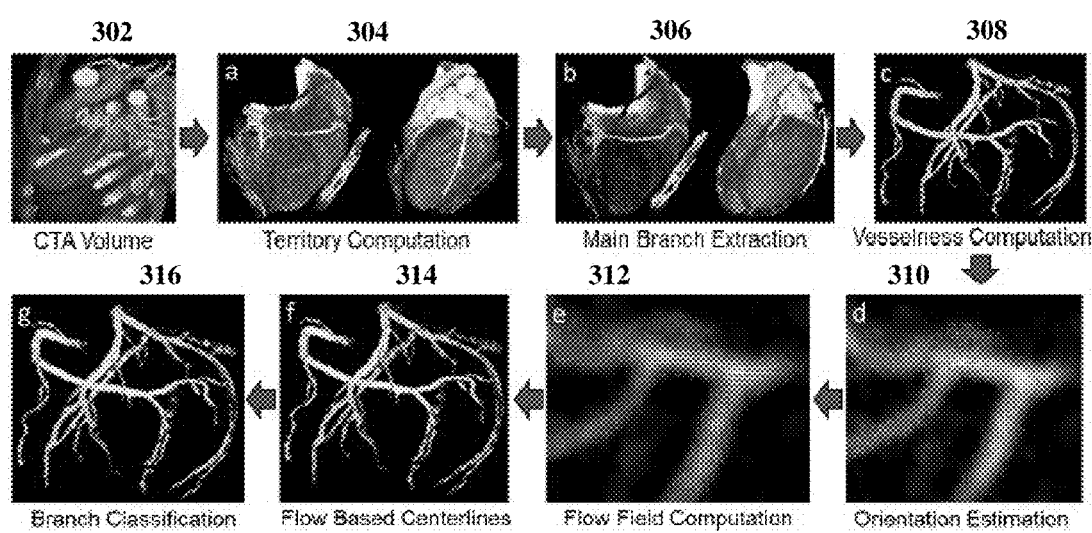
FIG. 3 illustrates exemplary results of methods steps of the method of FIG. 2.

FIG. 2 illustrates a method of extracting coronary artery centerlines from a computed tomography angiography (CTA) image according to an embodiment of the present invention. The method of FIG. 2 describes an embodiment in which coronary artery centerlines are extracted from a CTA image. It is to be understood that the method of FIG. 2 can be similarly applied to detect other type of vessels of interest (e.g., liver artery, renal artery, cerebral artery, etc.) from a CTA image or another type of medical image (e.g., 3D DynaCT, magnetic resonance angiography (MRA), digital subtraction angiography (DSA), 2D X-ray angiography, etc.). FIG. 3 illustrates exemplary results of methods steps of the method of FIG. 2.

Referring to FIG. 2, at step 202, a CTA image of a patient is received. The CTA image can be a 3D coronary CTA image that includes at least all of a portion of the coronary arteries of the patient. The CTA image can be received directly from a CT scanner or can be received by loading a previously stored CTA image or receiving an electronic transmission of a CTA image from a remote computer device. Referring to FIG. 3, image 302 shows a rendering of an exemplary 3D CTA image.

Returning to FIG. 2, at step 204, a coronary territory is defined in the CTA image. Coronary arteries lie roughly on the surface of the heart between the heart chambers and the pericardium. In an advantageous embodiment, the four heart chambers, the pericardium, and the aortic root are detected in the CTA image and used to define a coronary territory, and the training and detection are constrained to only voxels inside the coronary territory defined by the automatically detected heart chambers, pericardium, and aortic root structures. The use of the coronary territory to constrain the detection is advantageous in that it both improves runtime and achieves a reduced false positive rate by excluding non-coronary voxels outside the territory. Image 304 of FIG. 3 shows a coronary territory extracted from the 3D CTA image 302.

Figure 4:
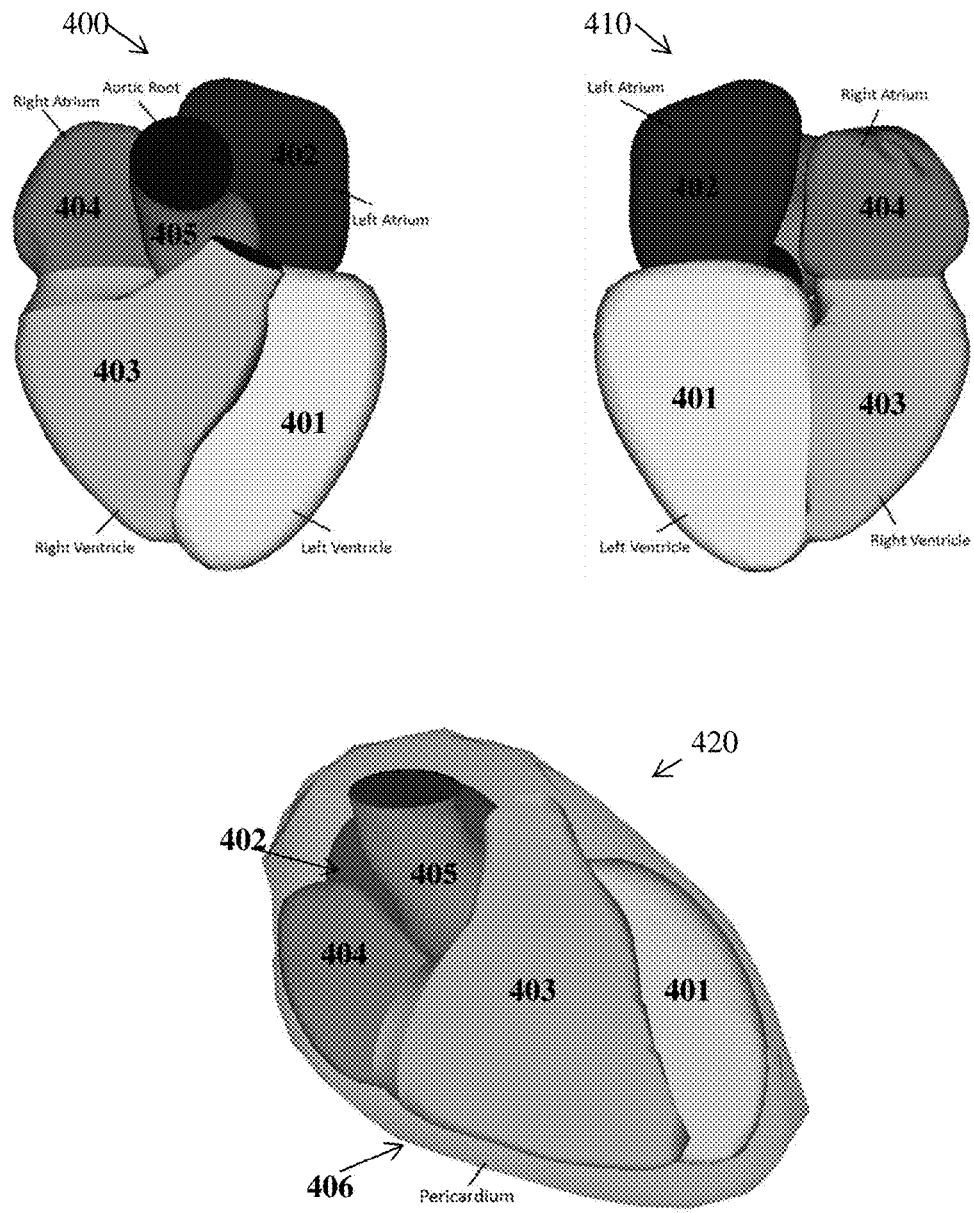
FIG. 4 illustrates an exemplary patient-specific heart model detected in a CTA image.
Figure 5:
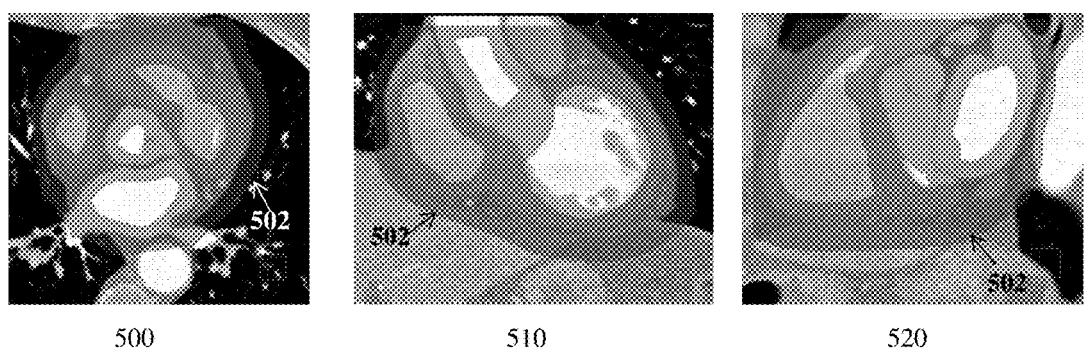
FIG. 5 illustrates an example of coronary territory defined in a CTA image.

A patient-specific heart model including four cardiac chambers, pericardium, and aortic root meshes can be automatically detected in CTA image using the methods described in U.S. Pat. No. 7,916,919, entitled "System and Method for Segmenting Chambers of a Heart in a Three Dimensional Image", U.S. Pat. No. 8,675,943, entitled "Method and System for Heart Isolation in Cardiac Computed Tomography Volumes for Patients with Coronary Artery Bypasses", and United States Patent Publication No. 2010/0239148, entitled "Method and System for Automatic Aorta Segmentation", the disclosures of which are incorporated herein by reference in their entirety. This detection can be performed as a preprocessing step and is very fast, i.e., taking about 3-4 seconds. FIG. 4 illustrates an exemplary patient-specific heart model detected in a CTA image. As shown in FIG. 4, images 400 and 410 show anterior and posterior views, respectively, of the patient-specific heart model including the detected left ventricle (LV) 401, left atrium (LA) 402, right ventricle (RV) 403, right atrium (RA) 404, and aortic root 405 meshes. Image 420 shows the detected pericardium mesh 406. A pericardium mask is defined by the detected pericardium mesh and a four chambers+aortic root mask is defined by the LV, LA, RV, RA, and aortic root meshes. The coronary territory can be defined inside the region between pericardium and four chambers+aortic root masks. However, in order to make the coronary territory more robust to errors in heart model detection, the four chambers+aortic root mask can be shrunk by a predetermined amount (e.g., 10 mm), the pericardium mask can be expanded by a predetermined amount (e.g., 10 mm), and the coronary territory can be defined inside the region between the expanded pericardium mask and the shrunk four chambers+aortic root mesh. FIG. 5 illustrates an example of coronary territory defined in a CTA image. As shown in FIG. 5 images 500, 510, and 520 show a coronary territory mask 502 overlaid on an axial multiplanar reconstruction (MPR) view, a coronal MPR view, and a sagittal MPR view, respectively, of a CTA volume. The predetermined size (e.g., 10-mm) band widths can be empirically tuned based on training datasets to make sure all coronaries in the training data are inside the coronary territory mask.

Although the use of the coronary territory improves runtime and reduces false positives, in other possible implementations, a coronary vesselness map can be detected without first defining the coronary territory by scanning all voxels in the input CTA image with a trained machine learning based classifier. In the case in which no coronary territory is defined, the vesselness classifier is also trained with negative training samples selected from outside of the coronary territory in training CTA images. It is to be understood, that for other types of vessels (e.g., liver arteries, renal arteries, cerebral arteries, etc.), a territory corresponding to the organ of interest can be defined or the vesselness map may be detected without being constrained to a particular territory in the medical image.

Returning to FIG. 2, at step 206, a coronary vesselness mask is generated in the defined coronary territory of the CTA image. In an advantageous embodiment, a vesselness based region growing method can be used to estimate the coronary vesselness mask. In a possible implementation, coronary artery ostia points can be detected as a byproduct of the aortic root detection described in United States Patent Publication No. 2010/0239148, entitled "Method and System for Automatic Aorta Segmentation", the disclosure of which is incorporated herein by reference in its entirety, and the coronary ostia points can be used as seed points for the vesselness based region growing. However, the region growing seeded at ostia points may terminate early at occluded coronaries with severe pathologies or imaging artifacts, such as motion artifacts. This could be a problem, especially, when the region growing terminates along a proximal part of a main branch, which could result in missing clinically important branches as well as their downstream tree. In an advantageous embodiment, in order to make the region growing more robust to occlusions, the main branches of the coronary arteries (e.g., right coronary artery (RCA), left anterior descending (LAD), and left circumflex (LCX)) can be initially detected, and the main branches can be used together with the coronary ostia points as seeds for the vesselness based region growing. The main branches of the coronary artery can be initially detected by initializing centerlines of the main coronary artery branches based on the segmented heart chambers using models of the main coronary artery branches learned from a training dataset and then locally refining the centerlines of the main coronary artery branches based in the image data, as described in U.S. Pat. No. 9,129,417, entitled "Method and System for Coronary Artery Centerline Extraction," the disclosure of which is incorporated herein by reference in its entirety. Image 306 of FIG. 3 illustrates main branches extracted in the coronary territory defined in image 304.

Figure 6:
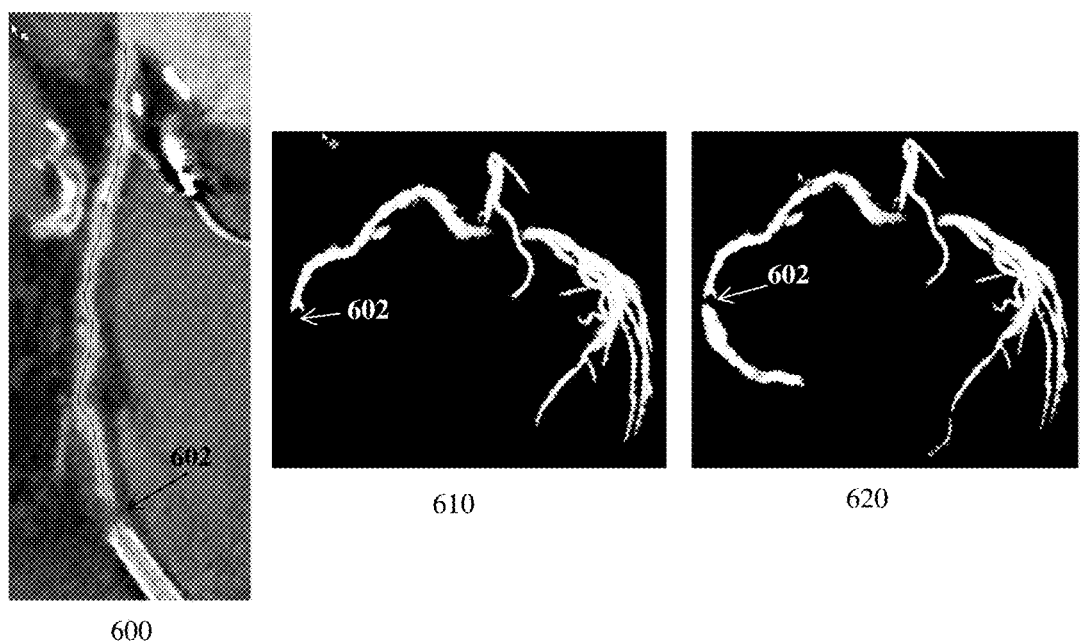
FIG. 6 illustrates exemplary coronary vesselness masks generated for a patient with a severe occlusion.

Using the detected main branch (e.g., RCA, LAD, and LCX) centerline points and the detected coronary ostia points as seed points, region growing can be performed starting from the voxels within a local neighborhood (e.g., 5 mm) of the seed points. In an exemplary implementation, the region growing uses 26 neighbor voxel connectivity and visits voxels with vesselness scores above a specified threshold. In order to prevent leakage to other structures, such as bones, the region growing can be constrained to only voxels within the defined coronary territory mask. In an advantageous implementation, the vesselness scores can be computed by a trained vesselness classifier on a voxel-by-voxel basis during the region growing propagation. Image 308 of FIG. 3 shows a coronary vesselness mask generated using vesselness based region growing based on the detected main coronary branches in image 306. FIG. 6 illustrates exemplary coronary vesselness masks generated for a patient with a severe occlusion. As shown in FIG. 6, image 600 shows a curved MPR visualization of a patient's RCA main branch with a severe occlusion 602, overlaid with the detected centerline of the RCA main branch. Image 610 shows a coronary vesselness mask extracted using vesselness based region growing seeded with only the coronary ostia points. As shown in image 610, the region growing seeded with only the coronary ostia points terminates early at the occlusion 602. Image 620 shows a coronary vesselness mask seeded with the detected centerline points of the RCA main branch, as well as the coronary ostia points. As shown in image 620, seeding with the detected main branch improves the region growing result by jumping over the occlusion 602. Accordingly, seeding with the detected main branches makes the region growing more robust to gaps due to severe occlusions or motion artifacts.

In an advantageous embodiment, the vesselness score for each voxel can be a machine learning based vesselness measure calculated for each voxel by a trained machine learning based vesselness classifier. For example, in a possible embodiment, the machine learning based vesselness measure can be calculated using a trained machine learning based vesselness classifier as described in U.S. Pat. No. 9,129,417, entitled "Method and System for Coronary Artery Centerline Extraction," the disclosure of which is incorporated herein by reference in its entirety. In another possible embodiment, the vesselness score can calculated for each voxel using a sequence of trained classifiers that calculate probability scores for the voxels based on image features and geometric features extracted for each voxel, as described in U.S. patent application Ser. No. 15/446,409, filed Mar. 1, 2017, entitled "Method and System for Machine Learning Based Estimation of Anisotropic Vessel Orientation Tensor", the disclosure of which is incorporated herein by reference in its entirety. Such a vesselness classifier is trained based on annotated training data in an offline training phase, and then the trained vesselness classifier is applied to calculate vesselness scores for the voxels of the received CTA image. In an advantageous implementation, in order to better tune feature parameters for different vessel scales, two separate vesselness classifiers are trained: one for small scale coronary arteries, and one for large scale coronary arteries. Vesselness scores can be calculated for each voxel using both the small scale and large scale vesselness classifiers, with the maximum of the small scale vesselness score and the large scale vesselness score being assigned as the final vesselness score for each voxel. The trained vesselness detector can calculate the vesselness score based on all or some combination of an anatomy context based geometric feature and image features including steerable features, intensity Hessian based vesselness, local intensity statistics, and gradient covariance based features extracted for a particular voxel. In an advantageous implementation, the sequence of trained classifiers can include a cascade of trained probabilistic boosting trees (PBTs), in which a first stage PBT classifies each voxel as positive or negative based on computationally inexpensive features (e.g., anatomy context based geometric feature and steerable features) and a second stage PBT calculates a vesselness score for voxels classified as positive by the first stage PBT based on the computationally inexpensive features and computational expensive features (e.g., intensity Hessian based vesselness, local intensity statistics, and gradient covariance based features).

Returning to FIG. 2, at step 208, vessel orientation tensors are estimated for voxels in the coronary vesselness mask. Vesselness measurements typically only generate a scalar value representing the probability for a voxel to be inside a vessel without an estimate of the vessel orientation. In an advantageous embodiment of the present invention, machine-learning based classification is used to predict an isotropic vessel orientation tensor at an image voxel that can be used to compute the likelihood of a particular direction being aligned with the true vessel orientation. Estimated vessel orientation tensors provide comprehensive orientation information, especially at bifurcations where vessels have more than one true orientation, and such orientation information can be used to guide centerline extraction. The vessel orientation tensors can be estimated using the method described in U.S. patent application Ser. No. 15/446,409, filed Mar. 1, 2017, entitled "Method and System for Machine Learning Based Estimation of Anisotropic Vessel Orientation Tensor", the disclosure of which is incorporated herein by reference in its entirety.

In an advantageous embodiment, a set of discrete orientations are constructed at each voxel based on the position of that voxel along with those of a subset of its neighboring voxels. In an exemplary implementation, all of the immediate neighbors of the voxel are used to define respective discrete orientations, resulting in a total of 26 voxels being used to construct the discrete orientations. In particular, each discrete orientation is defined as a direction from the voxel to a respective one of its neighboring voxels. Since the orientation is a symmetric measure, the vessel orientation tensor estimation method can consider only 13 non-symmetric discrete orientations from the set of 26 discrete orientations. Note that it is also possible to use a broader template of neighbors to construct denser discrete orientations. According to an advantageous embodiment, at a given image voxel, a trained vessel orientation tensor classifier predicts classification scores for each of the discrete orientations (e.g., the set of 13 non-symmetric discrete orientations) and the predicted classification scores of the discrete orientations are then used to construct an orientation tensor for that voxel. The trained vessel orientation tensor classifier can have the same or a similar structure as the vesselness classifier described above, but with sample patches oriented along discrete orientations. The training examples used to train the vessel orientation tensor classifier are sampled to learn both location and orientation instead of only location. In a possible implementation, separate small and large scale vessel orientation tensor classifiers can be trained and classification scores can be predicted at each voxel for both small and large scales in order to account for variation in coronary size.

The machine learning based classifier is trained to assign high probabilities to samples oriented along vessel direction at coronary voxels, and low probabilities to samples that have either false orientation or fall outside coronary lumen. In an exemplary implementation, expert annotated CTA datasets with whole left coronary artery (LCA) and right coronary artery (RCA) centerline trees can be used as training datasets. Each centerline tree includes densely sampled centerline points with a rough estimate of corresponding cross-sectional vessel radius. For training the vessel orientation tensor classifier, positive training examples are sampled for every voxel in the proximity of annotated coronary centerlines, e.g., voxels within a half radius range of the annotated coronary centerlines, where each positive example is assigned a discrete orientation that makes smallest angle with the true continuous vessel orientation. For negative training examples, all voxels inside the coronary lumen and within a certain size band around the lumen boundary can be sampled, and assigned the following sample orientations: If the voxel is within the band around the lumen boundary, all discrete orientations are used as negative training examples; Otherwise (i.e., for voxels inside the coronary lumen), discrete orientations that make an angle more than a certain degree (e.g., 45) with the true vessel orientation are used as negative training examples, in order not to confuse the classifier. The vessel orientation tensor classifier can be trained based on all or a subset of geometric and image features extracted from the training examples at their respective discrete orientations, including for example an anatomy context based geometric feature, steerable features, Hessian based vesselness, local intensity statistics, and gradient covariance based features. The vessel orientation tensor classifier can be trained using one or more PBTs. In a possible embodiment, the vessel orientation tensor classifier (for each the small and large scales) can be trained using a cascaded PBT structure that uses only inexpensive features (e.g., anatomy context based geometric feature and steerable features) to train a first stage PBT and uses the inexpensive features and expensive features (e.g., Hessian based vesselness, local intensity statistics, and gradient covariance based features) to train a second stage PBT. In a possible implementation, the vessel orientation tensor classifier may also include a third stage PBT trained using all of the features extracted from both the CTA image data and a probability map generated by the second stage PBT.

Figure 7:
FIG. 7 illustrates exemplary results of estimating vessel orientation tensors of a coronary artery in a CTA image.
Figure 7:
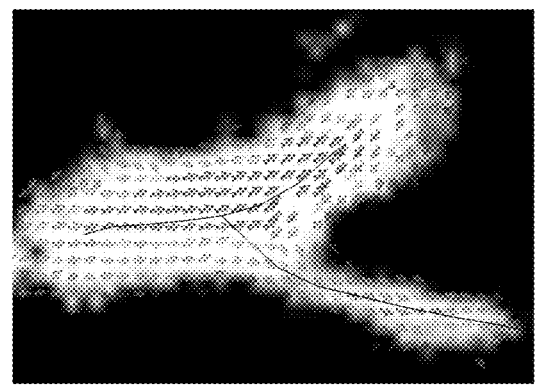

At each voxel in the coronary vesselness map, a classification score is calculated for each of the plurality of discrete orientations using the trained vessel orientation tensor classifier. At a given voxel, each of the plurality of discrete orientations is treated as an independent sample that is classified by the trained vessel orientation tensor classifier based on the features extracted for that discrete orientation (i.e., from image patches aligned with that discrete orientation) at that voxel. Accordingly, the trained vessel orientation tensor classifier calculates a respective probabilistic classification score for each discrete orientation at each voxel. A vessel orientation tensor K at each voxel is calculated based on the classification scores of the plurality of discrete orientations at that voxel. In an advantageous embodiment, at a given voxel, the classification scores calculated for each of the plurality of discrete directions are used to scale corresponding unit orientation vectors for the plurality of discrete directions and their symmetric directions, and a tensor K is calculated as the covariance of the scaled vectors. Suppose that $s_1, s_2, \ldots, s_{13}$ are estimated classification scores for unit orientation vectors $\vec{d}_1, \vec{d}_2, \ldots, \vec{d}_{13}$, respectively, at a given voxel. The classification scores $s_1, s_2, \ldots, s_{13}$ are used to scale the respective unit orientations vectors $\vec{d}_1, \vec{d}_2, \ldots, \vec{d}_{13}$ and their respective symmetric directions $-\vec{d}_1, -\vec{d}_2, \ldots, -\vec{d}_{13}$. All of the scaled vector samples $\vec{d}_1 s_1, \vec{d}_2 s_2, \ldots, \vec{d}_{13} s_{13}$ and their symmetric directions $-\vec{d}_1 s_1, -\vec{d}_2 s_2, \ldots, -\vec{d}_{13} s_{13}$ can be represented as three dimensional points. The vessel orientation tensor K can then be defined as the covariance matrix of these three dimensional points. The vessel orientation tensor is both symmetric and positive definite. FIG. 7 illustrates exemplary results of estimating vessel orientation tensors of a coronary artery in a CTA image. As shown in FIG. 7, image 700 shows a 3D visualization of detected coronary voxels overlaid with an annotated left coronary artery (LCA) tree. Image 710 shows an MPR view of a portion of the LCA overlaid with the principal component of detected vessel orientation tensors. It can be noted that since the vessel orientation is a symmetric measure, the orientation the arrows in image 710 indicates the local vessel orientations but the specific direction the arrows are pointing can be ignored. That is, arrows pointing in symmetric/opposite directions along the same orientation can be considered to be equivalent. An intensity or color of each arrow can indicate a tensor magnitude (e.g. first principal component or norm). Image 310 of FIG. 3 shows a principal component of estimated vessel orientation tensors around of a second diagonal bifurcation of the left anterior descending (LAD) coronary artery.

Figure 8:
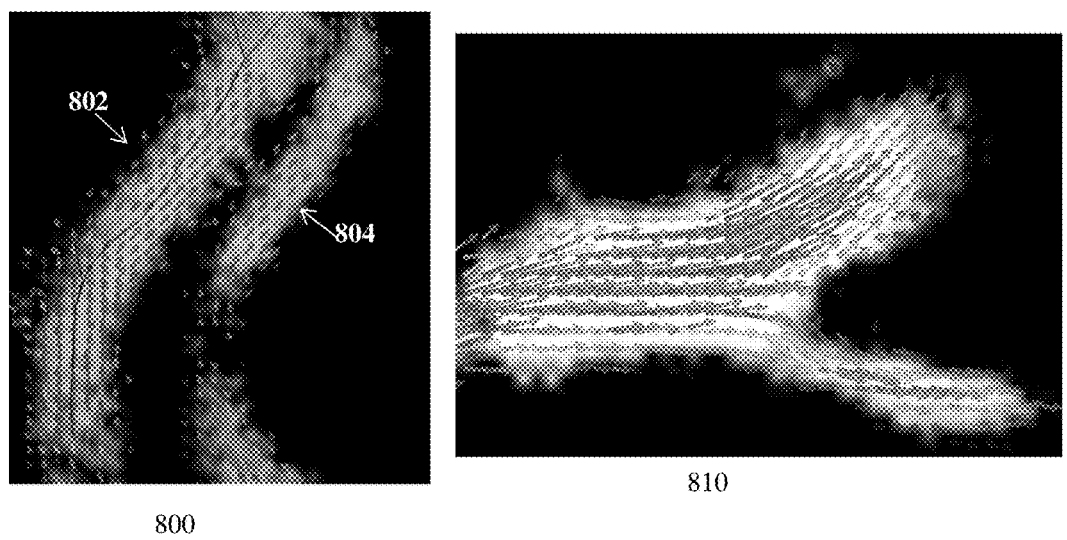
FIG. 8 illustrates examples of flow fields computed based on vessel orientation tensors in coronary vesselness maps.

Returning to FIG. 2, at step 210, a flow field is estimated for the voxels in the coronary vesselness mask based on the estimated vessel orientation tensors. In an advantageous embodiment, the flow field is estimated using an analogy of fluid flowing from regions of high pressure by computing a fluid flow simulation where the coronary ostia are specified as a high pressure region. For each coronary tree, an incompressible inviscid steady state porous media flow is computed inside the detected vesselness mask with boundary conditions on pressure. The flow computation treats the mask voxels as a porous material with a voxel permeability. In this context, the permeability can be understood as an inverse resistance to flow in the voxel. The principal directions of the estimated vessel orientation tensor and its eigenvalues at a given voxel relate the ease of flowing along each direction at the voxel, giving a local anisotropic structure. The voxels in the vicinity (e.g., 5 mm) of the ostium points are considered as inlet points with high permeability. However, outlet points corresponding to coronary distal points are not known a priori unless provided by an operator or another algorithm. Therefore, all voxels along the mask are considered as outlet points with low permeability, or equivalently, high resistance to ensure that most of the flow stays within the vascular structures. The pressure is forced to be unit for inlet voxels and zero outside the mask. In an advantageous embodiment, instead of a fixed uniform isotropic permeability, the estimated vessel orientation tensors are used as permeability tensors. The flow can be efficiently computed by solving a tensor weighted Laplacian model $\nabla \cdot (K \nabla p)=0$, where K is the estimated vessel orientation tensor and p denotes pressure. FIG. 8 illustrates examples of flow fields computed based on vessel orientation tensors in coronary vesselness maps. As shown in FIG. 8, image 800 shows an estimated flow field in a coronary artery branch 802 and an adjacent vein 804, and image 810 shows an estimated flow field in a coronary artery branch with a bifurcation. The color or intensity of the arrows represents the velocity magnitudes.

Using the estimated coronary orientation tensors as permeability tensors has several advantages. Since the vessel orientation tensor is lower along directions that are not aligned with true coronary orientation, the computed flow is forced to be low between coronaries and touching structures. This makes this coronary centerline extraction approach robust to leaking into adjacent structures, as shown in image 800 of FIG. 8. Further, the magnitude of the vessel orientation tensor based permeability is higher in the coronary center and gradually decreases towards background. Therefore, the velocities in the computed flow vary from low at the walls and background to a maximum along the coronary center, which makes it advantageous to use for centerline tracing. In addition, as shown in image 810 of FIG. 8, anisotropy of the vessel orientation tensors yield natural flow fields in bifurcation regions for which common centerline metrics are not well-defined. Image 312 of FIG. 3 shows a flow field at the second diagonal bifurcation of the LAD computed based on the estimated vessel orientation tensors shown in image 310.

Figure 9:
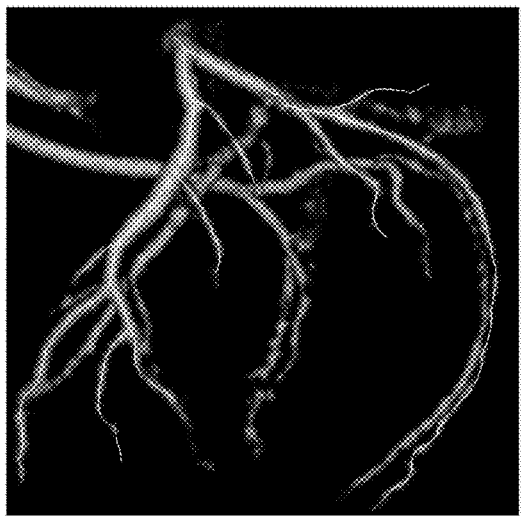
FIG. 9 illustrates exemplary coronary artery centerlines detected by finding a maximal flow path.
Figure 9:
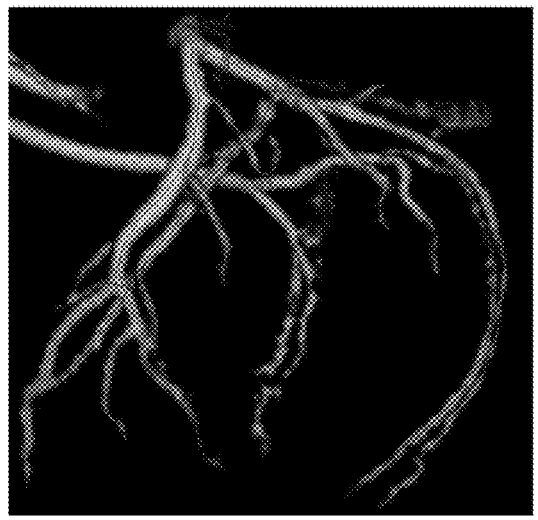

Returning to FIG. 2, at step 212, the coronary artery centerline is extracted based on the estimated flow field by finding a path that carries maximum flow. In advantageous embodiment of the present invention, which overcomes the centerline shortcut problem prevalent in other centerline extraction techniques, the computed flow field is used for centerline tracing by maximizing the flow carried along paths through the coronary artery. The centerline between any two locations is defined as the path that carries maximum amount of flow between the two locations. The problem of finding maximum flow path can be formulated as finding a "widest path/maximum bottleneck path" in a directed discrete graph with nodes corresponding to image voxels and directed edges connecting these nodes with their capacities from cross-sectional flow rates computed along the edge directions. The direction of the edges are determined from the pressure field, i.e., from high to low pressure. Efficient algorithms exist to solve widest path problem in a directed graph. For extracting the full coronary centerline tree inside the vesselness mask, we compute the maximum flow path from detected ostium to each voxel in the mask and iteratively pick the path that has maximum flow volume, i.e., integral of flow-rate along the path. That is, let G=(V, E) be a directed graph with vertices V corresponding to image voxels and directed edges E connecting vertices from high pressure to low pressure. Each edge is assigned a weight based on the cross-sectional flow rates computed along that edge. The maximum flow path between two vertices in this directed graph can be computed by finding the widest path which maximizes the weight of the minimum weight edge along the path. In an exemplary implementation, single source widest path in a directed graph can be solved efficiently by a modified Dijkstra's algorithm if the edge weights are sorted, which is satisfied by this graph because of conservation of flow rates. To obtain the centerline tree, the widest paths from the coronary ostium to all vertices in the graph are considered the path that has a maximum flow volume, i.e., the integral of the flow rate along the path, is iteratively selected for each respective vertex. Paths with length below a saliency threshold may be pruned away. The saliency threshold may be defined as a length-scale ratio. FIG. 9 illustrates exemplary coronary artery centerlines detected by finding a maximal flow path. As shown in FIG. 9, image 900 shows ground truth centerlines overlaid on a coronary vesselness mask of a CTA image, and image 910 shows coronary artery centerlines extracted by detecting based on an estimated flow field by detecting a path that carries maximum flow. It can be observed in image 910, that the centerline tracing accuracy is improved with respect to the coronary artery centerlines extracted using a shortest path algorithm shown in image 110 of FIG. 1. Image 314 of FIG. 3 shows flow-based extracted coronary artery centerlines.

Figure 10:
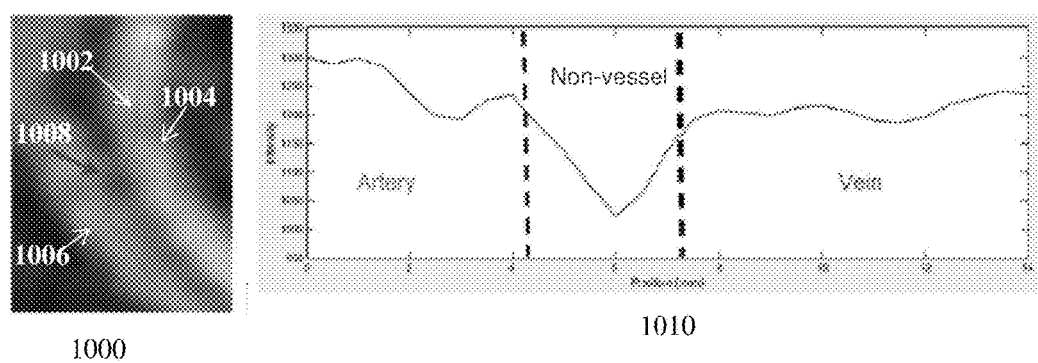
FIG. 10 illustrates an example of a detected centerline of a coronary artery leaking into an adjacent vein.

Returning to FIG. 2, at step 214, branches of the coronary artery centerline are pruned using machine learning based classification. The flow based coronary artery centerlines are detected with a very high sensitivity, but may result in detection of false branches. A machine learning based classification approach can be used to distinguish true coronary artery centerlines from false positive centerlines detected due to leakage. Existing learning based methods use support vector machines, probabilistic boosting trees, or random forest classifiers with a set of hand-crafted features, such as simple statistics or histogram computed for various profiles along a branch segment, e.g., intensity, gradient, diameter, and curvature. However, statistical or histogram features cannot accurately capture when a detected coronary artery centerline leaks into an adjacent vein, going through only a small non-vessel region. FIG. 10 illustrates an example of a detected centerline of a coronary artery leaking into an adjacent vein. Image 1000 of FIG. 10 shows a curved multi-planar reconstruction (MPR) visualization of a detected centerline 1002 of a coronary artery 1004 leaking from the coronary artery 1004 into an adjacent vein 1006. The detected centerline 1002 passes through a small non-vessel region 1008 between the coronary artery 1004 and the vein 1006. Image 1010 shows an intensity signal along the detected branch segment. As shown in image 1010, the intensity signal drops in the non-vessel region, but the intensity is similar in the coronary artery 1004 and in the vein 1006. Accordingly, statistical or histogram features may not accurately capture the small non-vessel sections. In addition, the location of a non-vessel region along the branch segment may vary depending on how the segment is sampled. Therefore, it is difficult to design hand-crafted features to train reliable branch classifiers.

In an advantageous embodiment of the present invention, deep learning is utilized to train a branch classifier using multi-channel one-dimensional (1D) input sampled along a vessel branch. For example, a convolutional neural network (CNN) can be used to learn the branch classifier. The CNN input channels include a plurality of 1D profiles sampled along the vessel branch, such as vessel scale, image intensity, centerline curvature, tubularity measure, intensity and gradient statistics (mean, standard deviation) along and inside cross-sectional circular boundary, and distance to a most proximal point in the branch. Rather than extracting hand-crafted features from these 1D profiles, the profiles are fed directly into the CNN classifier in order for the CNN to learn the best discriminative features from the profiles. Since the CNN can learn global features from local features inside sub-regions, the trained classifier can capture small non-vessel regions along a detected branch, which is difficult to achieve with statistical or histogram based features. Because of the translation invariant property of CNNs, by means of weight sharing and pooling layers, the classification using the CNN is robust to the location of a false section along the branch. The use of the multi-channel 1D input makes the training less prone to overfitting.

Figure 11:
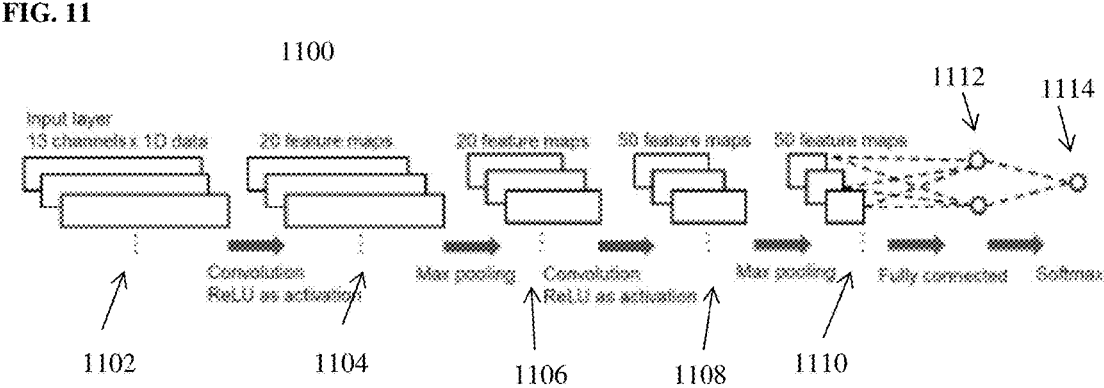
FIG. 11 illustrates an exemplary structure of a CNN for classification of vascular branches according to an embodiment of the present invention.

FIG. 11 illustrates an exemplary structure of a CNN for classification of vascular branches according to an embodiment of the present invention. As shown in FIG. 11, the CNN 1100 includes an input layer 1102, five hidden layers 1104, 1106, 1108, 1110, and 1112, and an output layer 1114. The input layer 1102 inputs 13 channels of 1D data sampled along a branch segment. In an exemplary implementation, the following 13 values are calculated at each sampling point along the branch, resulting 13 1D profiles that are input to the CNN: vessel scale, image intensity, centerline curvature, tubularity measure, intensity mean along cross-sectional circular boundary, intensity standard deviation along cross-sectional circular boundary, intensity mean inside cross-section circular boundary, intensity standard deviation inside cross-section circular boundary, gradient mean along cross-sectional circular boundary, gradient standard deviation along cross-sectional circular boundary, gradient mean inside cross-section circular boundary, gradient standard deviation inside cross-section circular boundary, and distance to the most proximal point in the branch. The input layer 1102 is followed by a convolution layer 1104 which uses a rectified linear unit (ReLU) activation function, followed by a max pooling layer 1106, followed by another convolution layer 1108 with a ReLU activation function, another max pooling layer 1110, a fully connected layer 1112, and the output layer 1114 that applies a softmax function to fully connected layer 1112 to compute a probability score for the branch segment. In the CNN 1100 of FIG. 11, layers 1104 and 1106 each generate 20 feature maps and layers 1108 and 1110 each generate 50 feature maps, but the present invention is not limited thereto. The fully connected layer 1112 includes a respective node for each possible class to which the branch segment can be classified.

The CNN assigns probabilistic scores to overlapping fixed length branch segments sampled along a vessel centerline from ostia to distal endpoints. The CNN classifier is trained to assign high probability scores to branch segments that fully overlap with the target vessels (e.g., coronary arteries) and low probability scores to branch segments that are fully or partially not part of the target vessels. The CNN can be trained using a gradient descent backpropagation technique based on annotated training datasets. For example, for coronary artery classification, the CNN can be trained based on expert annotated computer tomography angiography (CTA) datasets with the whole left coronary artery (LCA) and right coronary artery (RCA) centerline trees. Each centerline tree includes densely sampled centerline points with a rough estimate of a corresponding cross-sectional vessel radius at each centerline point. Overlapping fixed length branch segments are sampled along each centerline tree and multiple 1D profiles are computed for each branch segment. To train the classifier classes are assigned to the branch segments based on the overlap between the annotations and centerlines detected using an automated centerline detection algorithm, and gradient descent propagation can be used to learn weights for the layers of the CNN to best classify the branch segments in the trained dataset based on the multi-channel 1D inputs for the branch segments.

Once a flow based coronary centerline tree is extracted (in step 212 of FIG. 2), overlapping fixed size branch segments are sampled along each branch of the detected centerline tree. Each fixed size branch segment includes a plurality of centerline points, and the fixed size branch segments overlap such that a number of the centerline points in each fixed sized branch segment are also included in an adjacent fixed sized branch segment. For example, a new branch segment can be sampled starting at each centerline point along each branch of the detected centerline tree or starting at every other centerline point along the each branch of the detected centerline tree. In an exemplary implementation, the fixed length of the branch segments is 10 mm with 9 mm overlap between the branch segments. In this exemplary implementation, the centerline points are sampled every 0.5 mm along the centerline, therefore, a new branch segment is sampled starting at every other centerline point. The plurality of 1D profiles that correspond to the multi-channel input of the trained CNN classifier are extracted for each branch segment. The plurality of 1D profiles are measurements or features sampled along each branch segment. For example, 1D profiles of vessel scale, image intensity, centerline curvature, tubularity measure, intensity and gradient statistics (mean, standard deviation) along and inside cross-sectional circular boundary, and distance to a most proximal point in the branch can be extracted for each fixed length overlapping branch segment. For a given branch segment, each 1D profile is extracted by computing a value of the measurement or feature at each centerline point along the branch segment, resulting in a 1D vector of values. Accordingly, each 1D profile is a vector of values and each entry in the vector is a value of a particular measurement or feature at a respective point along the branch segment. A probability score is calculated for each branch segment based on the 1D profiles extracted for that branch segment, using the trained CNN classifier. The probability score calculated by the trained CNN classifier for a particular branch segment represents a probability that the branch segment is fully part of the vessel of interest (e.g., coronary artery). A final probability score is then assigned to each centerline point in the detected vessel centerline tree based on the probability scores of the overlapping branch segments containing that centerline point. For example, the final probability score assigned to a particular centerline point can be the maximum probability score among all of the branch segments containing that centerline point. Alternatively, the final probability score assigned to a particular centerline point can be the average of the probability scores of all of the branch segments containing that centerline point.

Median filtering with a small kernel can be applied to the final probability scores along the branches of the detected centerline tree to remove noisy detections. The final centerline tree is then obtained by pruning the detected centerline tree based on the final probability scores of the centerline points in the detected centerline tree. In a possible implementation, the final centerline tree can be obtained by pruning downstream of points that have final probability scores below a threshold value. Alternatively, each branch of the detected centerline tree can be pruned independently, and then the independently pruned branches can be merged to obtain the final vessel centerline tree. Each centerline point of a particular branch can be classified as vessel or non-vessel based on the final probability score. In one embodiment, a pruning point at which to prune the branch can be determined by pruning the branch at the first centerline point classified as non-vessel proximally. In another embodiment, the pruning point can be determined by pruning the branch at the first centerline point classified as vessel distally. In another embodiment, a pruning point is found for a vessel branch that minimizes a total error made by pruning the branch. In this embodiment, each centerline point in the detected vessel branch is classified as vessel or non-vessel based on the final probability scores, and for each centerline point in the detected vessel branch, an error value is computed by summing a count of upstream points (i.e., in a proximal direction) classified as non-vessel and a count of downstream points (i.e., in a distal direction) classified as vessel. The centerline point with the smallest error value is selected as the pruning point and the branch is pruned at that point. In an advantageous implementation, in order to make the pruning step robust to occlusions due to pathologies or image artifacts, the pruning may not be performed along the main coronary artery branches (RCA, LAD, and LCX), and is instead performed on branches downstream of the main coronary artery branches. Additional details regarding pruning the detected centerline using machine learning based classification of vessel branches to distinguish falsely detected branches from true branches are described in U.S. patent application Ser. No. 15/446,252, filed Mar. 1, 2017, entitled "Method and System for Machine Learning Based Classification of Vascular Branches," the disclosure of which is incorporated herein by reference in its entirety.

Figure 12:
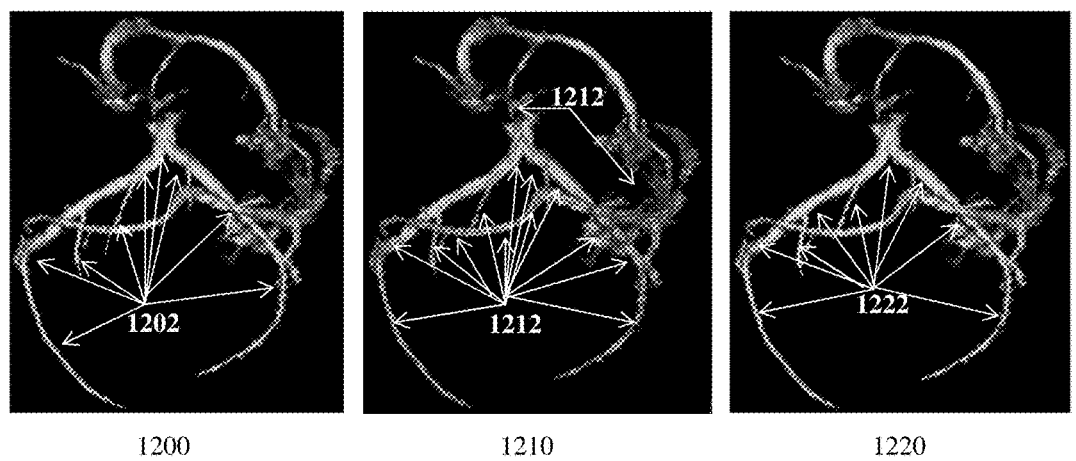
FIG. 12 illustrates exemplary results of pruning detected coronary artery centerlines using machine learning based classification.

FIG. 12 illustrates exemplary results of pruning detected coronary artery centerlines using machine learning based classification. As shown in FIG. 12, image 1200 shows ground truth expert annotated coronary artery centerlines 1202 overlaid on a VRT rendering of a vesselness mask detected in a 3D coronary CTA image. Image 1210 shows detected coronary artery centerlines 1212 extracted from the 3D CTA image using an automated centerline extraction method. Image 1220 shows the final detected coronary artery centerlines 1222 after pruning. It can be observed from the final pruned detected coronary artery centerline 1222 in image 1220 that the pruning removed falsely detected coronary artery centerlines from the detected coronary artery centerline 1212 in image 1210.

Returning to FIG. 2, at step 216, the detected coronary artery centerline is output. In particular, once the flow based detected coronary artery centerline is pruned, the final pruned coronary artery centerline tree is output. The final coronary artery centerline can be output by displaying the final coronary artery centerline on a display device of a computer system. Referring to FIG. 3, image 316 shows the final coronary artery centerline resulting from pruning the detected flow based coronary artery centerlines in image 314 using machine learning based branch classification. In addition to displaying the extracted coronary artery centerline, the coronary arteries can be segmented along the final pruned centerline tree, and the segmented coronary arteries can be displayed on a display device.

The method of FIG. 2 utilizes a fluid flow analogy to extract coronary artery centerlines. Embodiments of the present invention may use other possible physics based approximations for extracting centerlines of vascular structures. For example, it is possible to use steady-state heat transfer analogies to solve anisotropic Laplace or Poisson equations. Such models can also be solved in a transient setting, resulting in reaction-diffusion models and region-growing approaches. Another alternative is to use multi-phase flow models where one of the phases is injected along the model inlet. The model can be formulated such that the surface tension and other forces result in phase separation along the coronary lumen and a centerline can be defined using the flow of the fluid.

Recently, many advances have been made in designing machine learning algorithms which are trained on the results of computational simulations. In a possible embodiment, an offline training procedure can be used to build a machine learning model, which maps the image features to either the results of the physics based model (i.e., the estimated flow field), or even directly to the growth of the centerline. This approach is possible with many varieties of learning algorithms, including deep and recurrent neural networks and kernel-based methods. The machine learning model also has an advantage of having extremely fast computations for computing centerlines once the model has been trained.

The physics based models can be enriched by adding additional terms in the differential equations to result in desired structure of the centerline. For instance, in the flow-based analogy described above, the image gradients can be used to obtain "force" terms for the fluid flow equations. The magnitude of these force terms can be computed using models based on the local image structure. In an exemplary implementation, the deviation of the local distribution of intensity values with respect to a desired distribution, such as a healthy lumen, can be computed. The forces are then taken to be proportional to the computed deviation. In another possible implementation, a machine learning model is trained to predict a desired forcing term by training the machine learning model over either clinical datasets or synthetically designed datasets.

Figure 13:
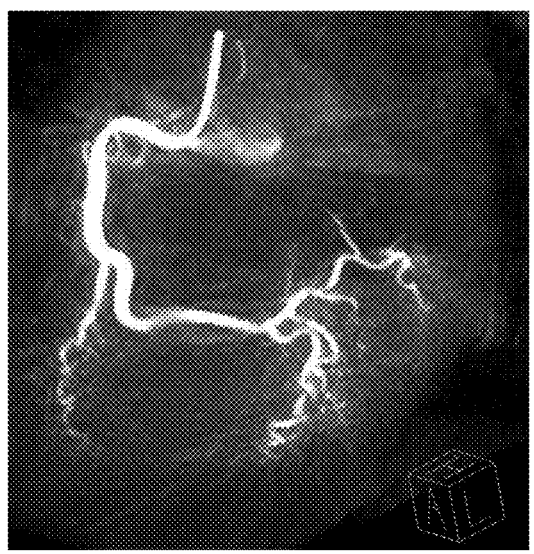
FIG. 13 illustrates exemplary results of coronary artery extraction in a 3D DynaCT image.
Figure 13:
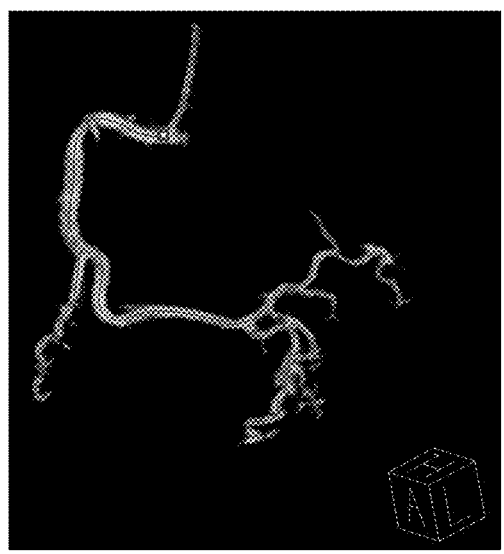

Although the method of FIG. 2 describes the application of extracting coronary arteries from a CTA image, this flow based vessel centerline extraction method can be similarly applied to any other vascular anatomies such as carotids, pulmonary, peripheral, and cerebral vessels, and to any other imaging modalities such as 3D DynaCT, magnetic resonance angiography (MRA), and digital subtraction angiography (DSA) if relevant medical data are provided for training. FIG. 13 illustrates exemplary results of coronary artery extraction in a 3D DynaCT image. As shown in FIG. 13, image 1300 shows an exemplary 3D DynaCT image with selective contrast injection in the right coronary artery tree, and image 1310 shows a detected centerline of the right coronary artery tree overlaid on a vesselness mask of the 3D DynaCT image 1300. In addition, the above described method does not enforce any vessel shape assumption and can robustly trace vessels that deviate from a tubular shape such as in the presence of pathologies or bifurcation, unlike methods that use medialness cost metrics which heavily depend on a tubularity assumption.

Figure 14:
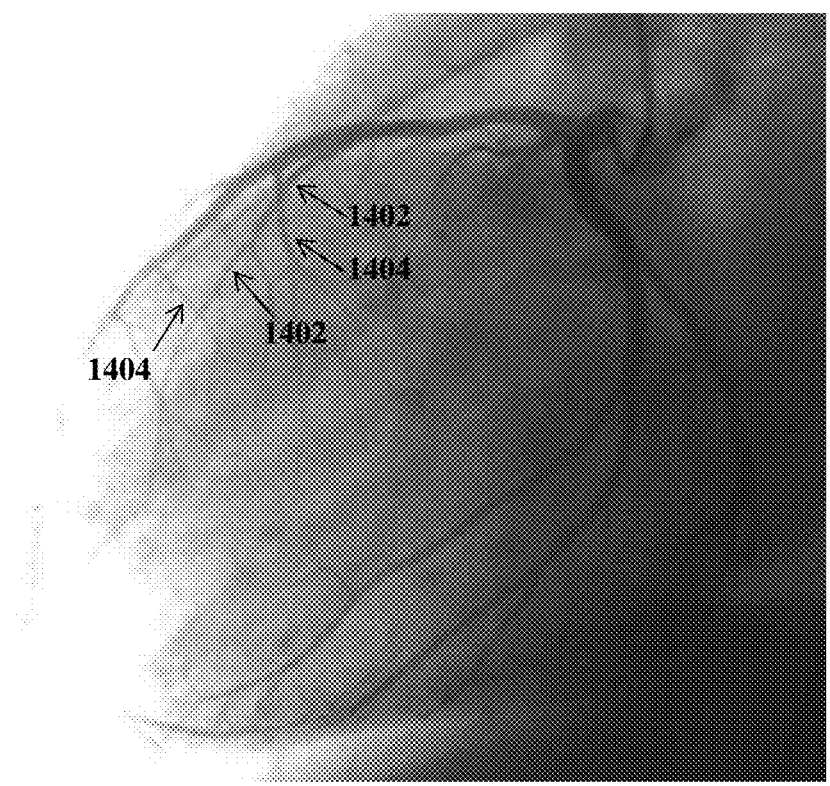
FIG. 14 illustrates an exemplary X-ray coronary angiography image with overlapping vessel branches.

The above described method for vessel centerline extraction is not limited to 3D medical image data and can be also applied to 2D medical image data, such as X-ray angiography, by computing the steady state flow using a 2×2 permeability tensor. Vessels in 2D X-ray angiography images usually overlap with each other which causes short-cut issues for centerline tracing algorithms. FIG. 14 illustrates an exemplary X-ray coronary angiography image with overlapping vessel branches. As shown in FIG. 14, the second diagonal branch of the left anterior descending (LAD) coronary artery 1402 overlaps with septal branches 1404. Since the above described centerline extraction method is based on flow computations, which is more natural than cost minimizing methods, the flow based centerline extraction method can successfully avoid short-cuts due to overlapping vessels in 2D X-ray angiography images.

Figure 15:
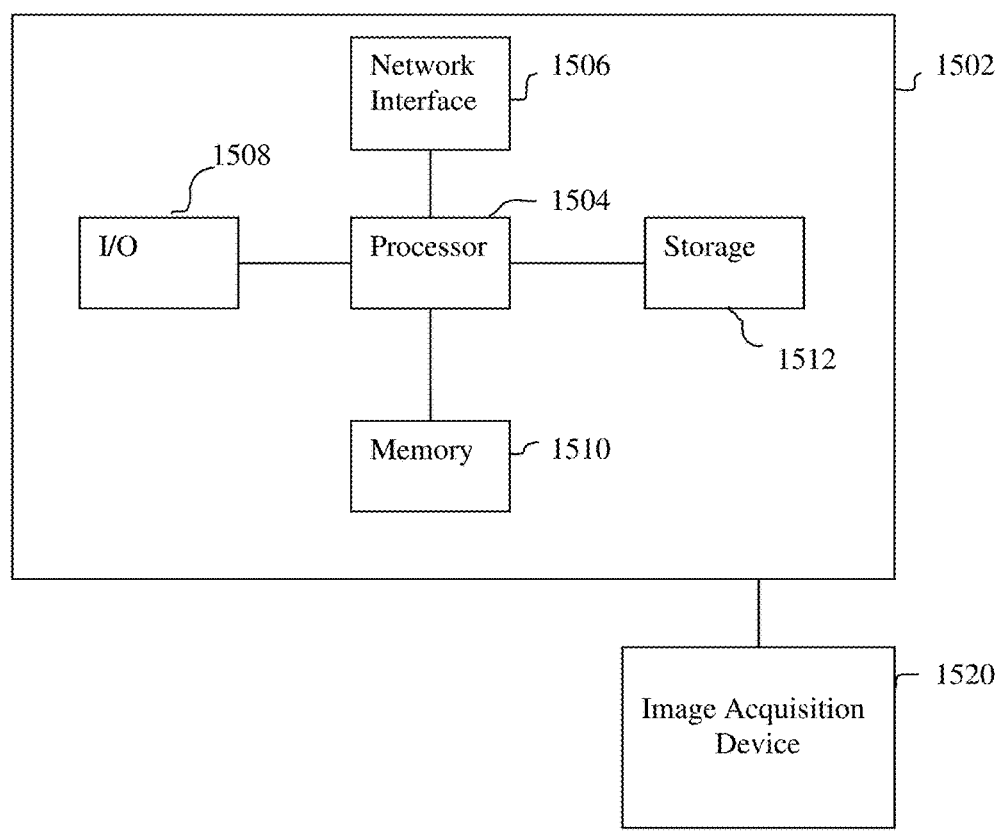
FIG. 15 is a high-level block diagram of a computer capable of implementing the present invention.

The above-described methods for extracting centerline representations of vascular structures via optimal paths in computational flow fields may be implemented on a computer using well-known computer processors, memory units, storage devices, computer software, and other components. A high-level block diagram of such a computer is illustrated in FIG. 15. Computer 1502 contains a processor 1504, which controls the overall operation of the computer 1502 by executing computer program instructions which define such operation. The computer program instructions may be stored in a storage device 1512 (e.g., magnetic disk) and loaded into memory 1510 when execution of the computer program instructions is desired. Thus, the steps of the method of FIG. 2 may be defined by the computer program instructions stored in the memory 1510 and/or storage 1512 and controlled by the processor 1504 executing the computer program instructions. An image acquisition device 1520, such as a CT scanner, can be connected to the computer 1502 to input image data to the computer 1502. It is possible to implement the image acquisition device 1520 and the computer 1502 as one device. It is also possible that the image acquisition device 1520 and the computer 1502 communicate wirelessly through a network. In a possible embodiment, the computer 1502 can be located remotely with respect to the image acquisition device 1520 and the method steps described herein can be performed as part of a server or cloud based service. In this case, the method steps may be performed on a single computer or distributed between multiple networked computers. The computer 1502 also includes one or more network interfaces 1506 for communicating with other devices via a network. The computer 1502 also includes other input/output devices 1508 that enable user interaction with the computer 1502 (e.g., display, keyboard, mouse, speakers, buttons, etc.). Such input/output devices 1508 may be used in conjunction with a set of computer programs as an annotation tool to annotate volumes received from the image acquisition device 1520. One skilled in the art will recognize that an implementation of an actual computer could contain other components as well, and that FIG. 15 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for extracting a centerline of a target vessel in a medical image of a patient, comprising:
    estimating a vessel orientation tensor for each of a plurality of voxels associated with the target vessel in the medical image using a trained vessel orientation tensor classifier;
    estimating a flow field for the plurality of voxels associated with the target vessel in the medical image based on the vessel orientation tensor estimated for each of the plurality of voxels; and
    extracting a centerline of the target vessel based on the estimated flow field for the plurality of voxels associated with the target vessel in the medical image by detecting a path that carries maximum flow.

2. The method of claim 1, wherein estimating a flow field for the plurality of voxels associated with the target vessel in the medical image based on the vessel orientation tensor estimated for each of the plurality of voxels comprises:
    estimating a flow at each of the plurality of voxels by simulating fluid flowing from a high pressure region to low pressure regions, where an ostium of the target vessel is set as the high pressure region.

3. The method of claim 2, wherein the plurality of voxels are voxels in a detected vesselness mask of the medical image, and estimating a flow at each of the plurality of voxels by simulating fluid flowing from a high pressure region to low pressure regions, where an ostium of the target vessel is set as the high pressure region comprises:
    computing an incompressible inviscid steady state porous media flow in the detected vesselness mask with boundary condition on the pressure, where each voxel of vesselness mask is assigned a tensor of permeability that defines an inverse resistance to flow in that voxel, wherein voxels in a pre-defined vicinity of the ostium of the target vessel are set as inlet points with high permeability, voxels along a boundary of the vesselness mask are set as outlet points with low permeability, and the estimated vessel orientation tensor is used as the tensor of permeability for each of the remaining voxels in the vesselness mask.

4. The method of claim 3, wherein the boundary conditions on the pressure force the pressure at the inlet voxels to be a unit pressure and the pressure outside the vesselness mask to be zero, and computing an incompressible inviscid steady state porous media flow in the detected vesselness mask with boundary condition on the pressure comprises:
    computing flow at each of the voxels in the vesselness mask by solving a tensor weighted Laplacian model.

5. The method of claim 1, wherein extracting a centerline of the target vessel based on the estimated flow field for the plurality of voxels associated with the target vessel in the medical image by detecting a path that carries maximum flow comprises:

generating a directed graph with vertices corresponding to the plurality of voxels and edges connecting the vertices, wherein each edge is assigned an edge weight based on a cross-section flow rate computed for that edge direction;

computing a respective maximum flow path between a vertex representing an ostium of the target vessel and each of the other vertices in the directed graph; and extracting the centerline of the target vessel by iteratively selecting, from the computed maximal flow paths, a path that has the maximal flow volume.

6. The method of claim 1, wherein extracting a centerline of the target vessel based on the estimated flow field for the plurality of voxels associated with the target vessel in the medical image by detecting a path that carries maximum flow comprises:

computing a respective maximal flow path from an ostium of the target vessel to each of the plurality of voxels; and extracting the centerline of the target vessel by iteratively selecting, from the maximal flow paths computed between the ostium and each of the plurality of voxels, a path having the maximum volume flow.

7. The method of claim 1, wherein estimating a vessel orientation tensor for each of a plurality of voxels associated with the target vessel in the medical image using a trained vessel orientation tensor classifier comprises:

calculating a classification score for each of a plurality of discrete orientations at each of the plurality of voxels based on features extracted from sampling patches oriented to each of the plurality of discrete orientations using the trained vessel orientation tensor classifier; and calculating the vessel orientation tensor for each of the plurality of voxels based on the classification scores of the plurality of discrete orientations at that voxel.

8. The method of claim 7, wherein calculating a classification score for each of a plurality of discrete orientations at each of the plurality of voxels based on features extracted from sampling patches oriented to each of the plurality of discrete orientations using the trained vessel orientation tensor classifier comprises, for each of the plurality of voxels:

scaling unit orientation vectors corresponding to the plurality of discrete orientations and symmetric directions to the plurality of discrete orientations using the classification scores of the plurality of discrete orientations at the voxel; and calculating the vessel orientation tensor at the voxel as a covariance matrix of the scaled unit orientation vectors.

9. The method of claim 1, further comprising:

detecting a vesselness map of the medical image, wherein the vesselness map of the medical image defines the plurality of voxels associated with the target vessel in the medical image.

10. The method of claim 1, further comprising:

pruning the extracted centerline of the target vessel using machine learning based classification of branches of the extracted centerline.

11. The method of claim 10, wherein pruning the extracted centerline of the target vessel using machine learning based classification of branches of the extracted centerline comprises:

sampling a plurality of overlapping fixed size branch segments from one or more branches of the extracted centerline of the target vessel;

extracting a plurality of 1D profiles along each of the plurality of overlapping fixed size branch segments;

calculating a probability score for each of the plurality of overlapping fixed size branch segments based on the plurality of 1D profiles using a trained deep neural network classifier;

assigning a final probability score to each of a plurality of centerline points in the one or more branches of the extracted centerline of the target vessel based on the probability scores of the overlapping fixed size branch segments containing that centerline point; and pruning the one or more branches of the extracted centerline of the target vessel based on the final probability scores of the plurality of centerline points in the one or more branches of the extracted centerline of the target vessel.

12. The method of claim 11, wherein the trained deep neural network is a trained convolutional neural network (CNN) that inputs the plurality of 1D profiles.

13. An apparatus for extracting a centerline of a target vessel in a medical image of a patient, comprising:

means for estimating a vessel orientation tensor for each of a plurality of voxels associated with the target vessel in the medical image using a trained vessel orientation tensor classifier;

means for estimating a flow field for the plurality of voxels associated with the target vessel in the medical image based on the vessel orientation tensor estimated for each of the plurality of voxels; and means for extracting a centerline of the target vessel based on the estimated flow field for the plurality of voxels associated with the target vessel in the medical image by detecting a path that carries maximum flow.

14. The apparatus of claim 13, wherein the means for estimating a flow field for the plurality of voxels associated with the target vessel in the medical image based on the vessel orientation tensor estimated for each of the plurality of voxels comprises:

means for estimating a flow at each of the plurality of voxels by simulating fluid flowing from a high pressure region to low pressure regions, where an ostium of the target vessel is set as the high pressure region.

15. The apparatus of claim 13, wherein the means for extracting a centerline of the target vessel based on the estimated flow field for the plurality of voxels associated with the target vessel in the medical image by detecting a path that carries maximum flow comprises:

means for computing a respective maximal flow path from an ostium of the target vessel to each of the plurality of voxels; and means for extracting the centerline of the target vessel by iteratively selecting, from the maximal flow paths computed between the ostium and each of the plurality of voxels, a path having the maximum volume flow.

16. The apparatus of claim 13, wherein the means for estimating a vessel orientation tensor for each of a plurality of voxels associated with the target vessel in the medical image using a trained vessel orientation tensor classifier comprises:

means for calculating a classification score for each of a plurality of discrete orientations at each of the plurality of voxels based on features extracted from sampling patches oriented to each of the plurality of discrete orientations using the trained vessel orientation tensor classifier; and means for calculating the vessel orientation tensor for each of the plurality of voxels based on the classification scores of the plurality of discrete orientations at that voxel.

17. The apparatus of claim 13, further comprising:
means for detecting a vesselness map of the medical image, wherein the vesselness map of the medical image defines the plurality of voxels associated with the target vessel in the medical image.

18. The apparatus of claim 13, further comprising:
means for pruning the extracted centerline of the target vessel using machine learning based classification of branches of the extracted centerline.

19. The apparatus of claim 18, wherein the means for pruning the extracted centerline of the target vessel using machine learning based classification of branches of the extracted centerline comprises:
means for sampling a plurality of overlapping fixed size branch segments from one or more branches of the extracted centerline of the target vessel;
means for extracting a plurality of 1D profiles along each of the plurality of overlapping fixed size branch segments;
means for calculating a probability score for each of the plurality of overlapping fixed size branch segments based on the plurality of 1D profiles using a trained deep neural network classifier;
means for assigning a final probability score to each of a plurality of centerline points in the one or more branches of the extracted centerline of the target vessel based on the probability scores of the overlapping fixed size branch segments containing that centerline point; and
means for pruning the one or more branches of the extracted centerline of the target vessel based on the final probability scores of the plurality of centerline points in the one or more branches of the extracted centerline of the target vessel.

20. A non-transitory computer readable medium storing computer program instructions for extracting a centerline of a target vessel in a medical image of a patient, the computer program instructions when executed by a processor cause the processor to perform operations comprising:
estimating a vessel orientation tensor for each of a plurality of voxels associated with the target vessel in the medical image using a trained vessel orientation tensor classifier;
estimating a flow field for the plurality of voxels associated with the target vessel in the medical image based on the vessel orientation tensor estimated for each of the plurality of voxels; and
extracting a centerline of the target vessel based on the estimated flow field for the plurality of voxels associated with the target vessel in the medical image by detecting a path that carries maximum flow.

21. The non-transitory computer readable medium of claim 20, wherein estimating a flow field for the plurality of voxels associated with the target vessel in the medical image based on the vessel orientation tensor estimated for each of the plurality of voxels comprises:
estimating a flow at each of the plurality of voxels by simulating fluid flowing from a high pressure region to low pressure regions, where an ostium of the target vessel is set as the high pressure region.

22. The non-transitory computer readable medium of claim 21, wherein the plurality of voxels are voxels in a detected vesselness mask of the medical image, and estimating a flow at each of the plurality of voxels by simulating fluid flowing from a high pressure region to low pressure regions, where an ostium of the target vessel is set as the high pressure region comprises:
computing an incompressible inviscid steady state porous media flow in the detected vesselness mask with boundary condition on the pressure, where each voxel of vesselness mask is assigned a tensor of permeability that defines an inverse resistance to flow in that voxel, wherein voxels in a pre-defined vicinity of the ostium of the target vessel are set as inlet points with high permeability, voxels along a boundary of the vesselness mask are set as outlet points with low permeability, and the estimated vessel orientation tensor is used as the tensor of permeability for each of the remaining voxels in the vesselness mask.

23. The non-transitory computer readable medium of claim 22, wherein the boundary conditions on the pressure force the pressure at the inlet voxels to be a unit pressure and the pressure outside the vesselness mask to be zero, and computing an incompressible inviscid steady state porous media flow in the detected vesselness mask with boundary condition on the pressure comprises:
computing flow at each of the voxels in the vesselness mask by solving a tensor weighted Laplacian model.

24. The non-transitory computer readable medium of claim 20, wherein extracting a centerline of the target vessel based on the estimated flow field for the plurality of voxels associated with the target vessel in the medical image by detecting a path that carries maximum flow comprises:
generating a directed graph with vertices corresponding to the plurality of voxels and edges connecting the vertices, wherein each edge is assigned an edge weight based on a cross-section flow rate computed for that edge direction;
computing a respective maximum flow path between a vertex representing an ostium of the target vessel and each of the other vertices in the directed graph; and
extracting the centerline of the target vessel by iteratively selecting, from the computed maximal flow paths, a path that has the maximal flow volume.

25. The non-transitory computer readable medium of claim 20, wherein extracting a centerline of the target vessel based on the estimated flow field for the plurality of voxels associated with the target vessel in the medical image by detecting a path that carries maximum flow comprises:
computing a respective maximal flow path from an ostium of the target vessel to each of the plurality of voxels; and
extracting the centerline of the target vessel by iteratively selecting, from the maximal flow paths computed between the ostium and each of the plurality of voxels, a path having the maximum volume flow.

26. The non-transitory computer readable medium of claim 20, wherein estimating a vessel orientation tensor for each of a plurality of voxels associated with the target vessel in the medical image using a trained vessel orientation tensor classifier comprises:
calculating a classification score for each of a plurality of discrete orientations at each of the plurality of voxels based on features extracted from sampling patches oriented to each of the plurality of discrete orientations using the trained vessel orientation tensor classifier; and
calculating the vessel orientation tensor for each of the plurality of voxels based on the classification scores of the plurality of discrete orientations at that voxel.

27. The non-transitory computer readable medium of claim 26, wherein calculating a classification score for each of a plurality of discrete orientations at each of the plurality of voxels based on features extracted from sampling patches oriented to each of the plurality of discrete orientations using the trained vessel orientation tensor classifier comprises, for each of the plurality of voxels:
   scaling unit orientation vectors corresponding to the plurality of discrete orientations and symmetric directions to the plurality of discrete orientations using the classification scores of the plurality of discrete orientations at the voxel; and
   calculating the vessel orientation tensor at the voxel as a covariance matrix of the scaled unit orientation vectors.

28. The non-transitory computer readable medium of claim 20, wherein the operations further comprise:
   detecting a vesselness map of the medical image, wherein the vesselness map of the medical image defines the plurality of voxels associated with the target vessel in the medical image.

29. The non-transitory computer readable medium of claim 20, wherein the operations further comprise:
   pruning the extracted centerline of the target vessel using machine learning based classification of branches of the extracted centerline.

30. The non-transitory computer readable medium of claim 29, wherein pruning the extracted centerline of the target vessel using machine learning based classification of branches of the extracted centerline comprises:
   sampling a plurality of overlapping fixed size branch segments from one or more branches of the extracted centerline of the target vessel;
   extracting a plurality of 1D profiles along each of the plurality of overlapping fixed size branch segments;
   calculating a probability score for each of the plurality of overlapping fixed size branch segments based on the plurality of 1D profiles using a trained deep neural network classifier;
   assigning a final probability score to each of a plurality of centerline points in the one or more branches of the extracted centerline of the target vessel based on the probability scores of the overlapping fixed size branch segments containing that centerline point; and
   pruning the one or more branches of the extracted centerline of the target vessel based on the final probability scores of the plurality of centerline points in the one or more branches of the extracted centerline of the target vessel.

31. The non-transitory computer readable medium of claim 30, wherein the trained deep neural network is a trained convolutional neural network (CNN) that inputs the plurality of 1D profiles.

* * * * *